United States Patent [19]

Heiny et al.

[11] Patent Number: 5,391,538
[45] Date of Patent: Feb. 21, 1995

[54] METHOD AND COMPOSITIONS FOR THE BIOLOGICAL CONTROL OF FIELD BINDWEED

[75] Inventors: Dana D. K. Heiny; George E. Templeton, II, both of Fayetteville, Ark.

[73] Assignee: Sandoz Ltd., Basel, Switzerland

[21] Appl. No.: 641,224

[22] Filed: Jan. 19, 1991

[51] Int. Cl.$^6$ ............................................. A01N 63/04
[52] U.S. Cl. ................................................... 504/117
[58] Field of Search ............................. 71/79; 504/117

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,390,360 | 6/1983 | Walker | 71/79 |
| 4,419,120 | 12/1983 | Walker | 71/79 |
| 4,776,873 | 10/1988 | Caulder et al. | 71/79 |

FOREIGN PATENT DOCUMENTS 0277736  8/1988  European Pat. Off. .

OTHER PUBLICATIONS

Heiny, "Phoma proboscis sp. nov. pathogenic on Convolvulus arvensis" Mycotaxin vol. 37 No. 2 pp. 457–471 Jan. 16, 1990.

*Westcott's Plant Disease Handbook*, 5th Ed. Van Nostrand Reinhold, New York, pp. 126, 127 and 172.

Host Specificity of Phoma Proboscis in the Convolvulaceae, Dana K. Heiny, American Phytopathology Society, Feb. 2–5, 1992.

Bottalico, A., et al. CAS 98:103,974y. *Phytopathol Mediterr.* 1982. 21(1), 39–40. "Identification of phomenone . . .".

Iacobellis, N. S., et al. CAS 105: 169,107n. *Phytopathol. Mediterr.* 1985, 24(3), 307–10. "Cytoganic effects of phomenone . . . ".

Nachmias, A., et al. CAS 88: 47,600c. *Physiol. Plant Pathol.* 1977, 10(2), 147–57. "Purification & characterization . . . ".

Primary Examiner—Glennon H. Hollrah
Assistant Examiner—S. Mark Clardy
Attorney, Agent, or Firm—Allen E. Norris

[57] ABSTRACT

Control of field bindweed employing a phytopathogenic fungus *Phoma proboscis*.

2 Claims, No Drawings

METHOD AND COMPOSITIONS FOR THE BIOLOGICAL CONTROL OF FIELD BINDWEED

FIELD OF THE INVENTION

The invention concerns a fungal pathogen *Phoma proboscis* Heiny, its use in a method for the control of field bindweed (*Convolvulus arvensis* L.) and compositions containing it.

DESCRIPTION OF THE PRIOR ART

The use of biological control in combatting weeds has become increasingly attractive in recent years due most particularly to its advantages with respect to environmental impact.

*Colletotrichum gloeosporiolds* f. sp. *aeschynomene* (Daniel et.al. U.S. Pat. No. 3,849,104) has been marketed commercially since 1982 for control of northern jointvetch in Arkansas rice fields. Chlamydospores of the fungus *Phytophthora palmivora* have been formulated for control of milkweed vine in Florida citrus groves (*Phytophthora palmivora*, Weed Science, W. H. Ridings, 1986, vol. 34, Suppl. 1, pp. 31–32). Unwanted persimmon trees in Oklahoma rangeland are controlled by hand inoculation with the wilt fungus *Acremonium diospyri* (C. A. Griffith, 1970 Samuel Roberts Noble Foundation, Inc., Ardmore, Okla.).

Other fungi with experimentally demonstrated potential for weed control include *Collectotrichum gloeosporioides* f. sp. *malvae* on round-leaved mallow (K. Mortensen, 1988, Weed Science, vol. 36, pp. 473–478 and CA Patent No. 517697); *Colletotrichum coccodes* on velvetleaf (Wymore et.al., 1987, Weed Science, vol. 35, pp. 377–383); *Colletotricum malvarum* on prickly sida (Templeton, U.S. Pat. No. 3,999,973); *Alternaria cassiae* on sicklepod, show crotalaria, and coffee senna (Walker, U.S. Pat. No. 4,390,360); *Fusarium lateritium* (Walker, U.S. Pat. 4,419,120); *Colletotrichum orbiculare* on spiny cocklebur (Auld et.al., 1988, Agriculture, Ecosystems, and Environment, vol. 21, pp. 219–223); *Cercospora rodmanii* on waterhyacinth (Conway et.al. U.S. Pat. No. 4,097,261); *Chondrostereum purpureum* on American blackcherry (de Jong et.al., 1990, Plant Disease, vol. 74, pp. 189–194); *Fusarium solani* f. sp. *cucurbitae* on Texas gourd (Wiedemann and Templeton, 1988, Plant Disease, vol. 72, pp. 36–38); *Fusarium roseum* "Culmorum" on *Hydrilla verticillata* (Charudattan, U.S. Pat. No. 4,263,036); and *Alternaria euphorbiicola* on *Euphorbia heterophylla* L. (Riley, U.S. Pat. No. 4,871,386).

Field bindweed occurs throughout the United States and in at least 43 other countries. The vines of this perennial plant climb around the stems of annual crops like cereals and sugar beets and infest fruit orchards, vineyards and other horticultural crops. At least 32 crops are affected throughout the world (L. G. Holm et.al., 1977, The World's Worst Weeds; Distribution and Biology, pp. 98–104). Field bindweed is not as much of a problem in the humid eastern United States as it is in the arid western U.S. (L. J. Meyer, 1978, North Central Weed Control Conference 33:141–142). In non-irrigated areas of low average precipitation, bindweed causes yield losses ranging from insignificant to complete crop failure (D. G. Swan, 1980, Washington State University, College of Agriculture Research Center Bulletin 0888). Heavy infestations can reduce winter wheat yields by one-third, and yields of other summer crops by three-quarters (W. M. Phillips, 1967, U.S.D.A. leaflet No. 496). Bindweed increases the time taken for pruning and picking. Fruit quality is reduced as bindweed shading prevents full color development in apples (J. G. Davison, 1976, Pesticide Science 7:429–435). During 1980, 2 million acres of crop land in California were infested by field bindweed, resulting in a total loss of about 25 million dollars (S. S. Rosenthal, 1983, California Agriculture 37:16–17). In cultivated fields, bindweed can produce 500,000 seeds per acre (Dow Chemical Company, 1989, AG Review, Special Bindweed June Issue Advertising Insert). Seeds can remain viable in soil for more than 20 years (F. Timmons, 1949, Agronomy Journal 41:130–133).

A deep and extensive root system with reserves that allow bud regeneration from the roots make bindweed difficult to kill and most chemical herbicide treatments require 3 to 5 years to kill mature field bindweed plants. The difficulty and expense of control of field bindweed by cultivation, competitive crops, and herbicides warrants emphasis on biological control efforts. Previous studies of biological control agents of field bindweed have focused mainly on insects. Many of these insect biocontrol agents have been disappointing because of lack of specificity (Rosenthal and Buckingham, 1982, Hilgardia, vol. 50, no. 2, pp. 1–19) or incomplete control (Wang and Kok, 1985, Biocontrol News and Information 6(4):303–310). A fungal plant pathogen, *Phomopsis convolvulus*, with potential for biological control was recently described on field bindweed (Ormeno-Nunez et.al., 1988, Plant Disease, vol. 72, pp. 338–342). The instant invention involves a different fungal species, *Phoma proboscis*, that gives excellent control and may have advantages, such as ease of spore production, over other species.

SUMMARY OF THE INVENTION

The instant invention concerns a method for the control of field bindweed, which comprises applying to the weed or the locus thereof a plant growth controlling amount of the fungus *Phoma proboscis* Heiny or a fungus having the identifying characteristics thereof or a mutation thereof.

This invention differs from the prior art in that this fungus is a new pathogen of field bindweed with particular requirements for large scale production, formulation and application. This pathogen can be formulated as a spray using a wettable powder and various spreader/sticker or emulsion additives obvious to those skilled in the art. The invention therefore also concerns a plant growth controlling composition comprising a plant growth controlling amount of the fungus *Phoma proboscis* or a fungus having the identifying characteristics thereof or a mutation thereof in admixture with an agriculturally acceptable carrier or adjuvant as well as biologically pure cultures of the fungus *Phoma proboscis* Heiny or a fungus having the identifying characteristics thereof or a mutation thereof.

DETAILED DESCRIPTION OF THE INVENTION

Dried, dead specimens of *Phoma proboscis* Heiny are on deposit in the U.S. National Fungus Collections (BPI ∩1103137) and the Herbarium of the Royal Botanic Gardens at Kew, England (K ∩H 288/90). Living specimens of *Phoma proboscis* Heiny were deposited in the Patent Depository of the American Type Culture Collection (ATCC ∩74032) on Jan. 8, 1991. The address of the American Type Culture Collection is:

B. A. Brandon, Associate Director for Administration, American Type Culture Collection, 12301 Parklawn Drive, Rockville, Md. 20852 U.S.A.

*Phoma proboscis* produces subglobose to flask-shaped, brown pycnidia measuring 173–550×112–275 μm (383×256 μm) with a neck or multiple necks from ⅓ to 3 times the diameter of the pycnidium. Conidia are salmon color in mass, otherwise hyaline, unicellular to occasionally one-septate, eguttulate, cylindrical or narrowly ellipsoidal, foot-shaped or sometimes slightly curved, obtuse at each end, measuring 5.5–15.0 (17)×2.3–5.0 μm, averaging 10.5×3.5 μm. In culture, unicellular, intercalary, spherical chlamydospore-like structures approximately 14 μm in diameter are produced. *Phoma proboscis* differs from other species in having rostrate pycnidia, relatively large eguttulate conidia that are occasionally septate, unicellular, spherical chlamydospores, and an optimum growth rate at cooler temperatures (20° C.).

*Phoma proboscis* was originally isolated from diseased field bindweed leaves and stems collected in Phillips County, Colorado. *Phoma proboscis* was not previously known to exist, and the pathogen had never been previously reported on the target weed. Abundant sporulation occurs following smearing of conidial suspensions on oatmeal agar (spread plate culture), and incubation under 12 hours per day of bright fluorescent light at 22°–24° C. for 5 to 7 days. For further characterization of *Phoma proboscis* of Heiny, Mycotaxon, v. 36, no. 2, pp. 457–471 1990 the contents of which are incorporated herein by reference.

*Phoma proboscis* is restricted in host range. Field bindweed and certain other members of the plant family Convolvulaceae and *Omphalodes linifolia* of the Boraginaceae are the only plant species out of 228 tested that are susceptible to the pathogen. The limited host range and highly virulent nature of *Phoma proboscis* indicate that this pathogen is selectively pathogenic to field bindweed and thus has potential for use as a biological control agent for field bindweed. The fungus has the specificity lacking in broad-spectrum chemical herbicides and insect pests previously investigated for bindweed control. The fungus has the potential to cause a secondary disease cycle that may provide residual control of shoots rebudding from the roots following initial die-back due to infection.

Spores of *Phoma proboscis* can be produced in submerged liquid culture. However, time must be allowed for pycnidia development on mycelial masses within the medium suspension.

*Phoma proboscis* may be used effectively as a mycoherbicide in diverse formulations, including agronomically acceptable adjuvants and carriers routinely utilized to facilitate dispersion of active ingredients over plant surfaces. Formulation, dosage, mode of application or other variables may affect mycoherbicide activity and will depend upon soil conditions, climate and other environmental considerations. The desired mode of application may warrant formulation in aqueous or non-aqueous media, as a dust, wettable powder, emulsifiable concentrate, granule or other type of formulation.

Conidia of *Phoma proboscis* are compatible with procedures that involve drying of spores for long term storage or ease of handling. Wet spores of *Phoma proboscis* may be mixed with various proportions of kaolin (clay) and air-dried with resultant high levels of germination (75–92%). The kaolin, or other extender, helps prevent mutual adherence of spores during drying, and facilitates suspension of spores upon re-addition of water. Spores can also be freeze-dried in double-strength skim milk and retain viability. Concentrated sugar solutions may be used for initial rehydration of spores to combat spore membrane disruption due to rapid osmotic changes that may occur in water alone.

Spreader/stickers may also enhance disease of field bindweed when added to spore suspensions of *Phoma proboscis* . Specifically 2% Activate 9–0 (complex blend of alkylpolyethoxyethanol, N-butanol, isopropanol, and dimethylpolystloxane, manufactured by Uniroyal Chemical, EPA Est. No. 7874-CA-1) or 1% Activate Plus (alkylarylpolyoxyethylene glycols, free fatty acids, and IPA, manufactured for Riverside/Terra Corp., Sioux City, Iowa 51101) added to spore suspensions increased necrosis of seedlings relative to treatments of spores alone without significant necrosis caused by the adjuvant alone.

Special formulations designed to improve stability (e.g. microcapsules) or to effect an environment for the fungus conducive to spore germination or to sporulation (of U.S. Pat. No. 4,902,333) may also be used.

In the control of field bindweed using *Phoma probocis* best results are obtained when the fungus infects plants at temperatures of from 16° to 28° C., preferably 20° to 24° . At 24° C. the fungus causes the most disease with dew periods of at least 12 hours at inoculum concentrations of $1\times10^5$ to $1\times10^9$ spores/ml or more in water. Spores are the preferred form of the fungus although mycelia may also be employed in sprays.

The fungus may be combined with spores of other biological control agents or with chemical control agents in a comprehensive or broad-spectrum approach to pest control whereby application rates of chemicals employed would be expected to be equal to or less than those employed conventionally. Applications of the fungus may also be made more than once during a growing season without the need for concern about run-off, drift or residue problems inherent to repeated chemical applications. The fungus is nontoxic to the applicator. The fungus might also be combined with other chemicals commonly used in farming operations, such as fertilizers, to minimize spray applications.

As used herein "plant growth controlling" is intended to mean the ability of the fungus according to the invention to infect its target plant *Convolvulus arvensis* L. to a degree sufficient to reduce or prevent the ability of that weed to detrimentally affect the growth of the crop plants which it normally infests.

The invention also includes other fungi having the identifying characteristics of *Phoma proboscis* or being mutations thereof particularly those retaining the ability to infect and control the growth of *Convolvulus arvensis* L.

EXAMPLE 1

Isolation

The fungal isolate designated C2K was obtained from infected field bindweed collected in Phillips County, Colo. Small pieces of lesions from field bindweed leaves, petioles, and stems are surface-sterilized for 5 minutes in 0.5% sodium hypochlorite, rinsed in sterile distilled water, and inserted into potato dextrose agar or placed on water agar. Plates are incubated at 24° C. with 12 hours of light each day, for 3 to 7 days. Fungi growing out of tissue or sporulating on it are individually transferred to nutrient media and allowed to grow and develop to maturity. Isolates are screened for pathogenicity by spray application of spores to individual pots of field bindweed seedlings, followed by 48 hours of dew at 24° C. Development of disease symptoms on seedlings is observed during the subsequent 2 weeks of incubation at 24° C. with a 14-hour photoperiod. The pathogenic isolate originally labeled C2K was determined to be the new species *Phoma proboscis* and was deposited with the American Type Culture Collection under accession no. ATCC 74032 on Jan. 8, 1991.

EXAMPLE 2

Spore Production and Harvest cultures are maintained on potato dextrose agar or oatmeal agar, but *Phoma proboscis* grows satisfactorily on various media in common use. For ease in pouring plates, one-half strength Difco oatmeal agar supplemented with agar is typically used (Difco Laboratories, Inc., Detroit, Mich. 48201). Uniform sporulation is attained by aseptically spreading water suspensions of conidia with a bent glass rod on acidified potato dextrose agar or oatmeal agar contained in Petri dishes and incubating for 5 to 7 days at 22° to 24° C. with a 12-hour photoperiod (Percival Mfg. Co. Culture Incubator Model I-35VL, Boone, Iowa 50036 or 42 cm from Bright Stik by General Electric, Cleveland, Ohio 44112).

Inoculum may be harvested by addition of several milliliters of distilled water to culture plates, scraping the surface of cultures with a glass microscope slide to break open pycnidia, allowing several minutes for conidia to ooze into the water, filtering through cheesecloth, and centrifuging to concentrate spores when necessary. Concentrations of conidial suspensions are adjusted based on hemacytometer counts. One spread plate typically yields $3 \times 10^8$ spores. Spore germination, determined by spreading 0.1 ml of a conidial suspension on 1.5% water agar is affected by spore concentration, temperature and time. Concentrations from $10^8$ to $10^9$ spores/ml have reduced germination relative to lower spore concentrations. At 24° C., spore concentrations of $4 \times 10^7$ spores/ml have greater than 90% germination after 9 hours. Germination of spores diluted and plated in a thin film of water in replicated Petri dishes without water agar for 15 hours at 24° C. under lights range from 87% at $10^4$ spores/ml to 9% at $10^7$ spores/ml, suggesting the presence of a germination inhibitor.

EXAMPLE 3

Epidemiology in Growth Chambers

The impact of disease caused by *Phoma proboscis* on field bindweed populations under controlled parameters of spore concentration (determined by use of a hemacytometer), dew period and temperature is investigated in plant growth chambers. Eight pots per treatment with ten seedlings each are inoculated by spraying with spore concentrations ranging from 0 to $10^9$ spores/ml and placed in dew for 12 hours at 20° or 24° C., followed by a 14-hour-per-day light exposure in a 24° C. growth chamber. Germination of conidia at the various concentrations on water agar is also assessed. After 2 weeks, average disease ratings are significantly greater ($P<0.005$) with each 10-fold increase in spore concentration up to $10^7$ spores/ml at both 20 and 24° C. No statistical difference is found between ratings of plants inoculated with $10^7$ or $10^8$ spores/ml. No significant difference is found between ratings of plants treated with $10^6$ or $10^9$ spores/ml. Disease at 20° C. is not significantly different from disease at 24° C. for all concentrations except $10^4$ ($P<0.01$). Increasing inoculum concentrations resulted in reduced fresh weights of shoots up to $10^7$ spores/ml. Optimum spore germination on water agar after 12 hours occurred at $10^5$ spores/ml for 20° C. and from $10^4$ through $10^7$ spores/ml for 24° C. Germination is greatly reduced at higher concentrations.

Dew period and temperature also affect disease development. For each of five temperatures, 27 pots containing 15 plants/pot are inoculated with $4\times10^7$ spores/ml, and 27 pots are not inoculated. All are placed in a dew chamber at the specified temperature: 16°, 20°, 24°, 28°, or 32° C. At 3-hour intervals up to 24 hours, and again at 48 hours, three inoculated pots, three noninoculated pots and conidial spread plates on water agar are removed and placed in a growth chamber with the same photoperiod temperature as the dew temperature. Disease ratings are recorded 1 week and 2 weeks after inoculation.

Disease severity caused by *Phoma proboscis* increases during the period between 1 and 2 week ratings at all temperatures except 32° C., at which little or no disease occurs. High levels of disease are achieved after 2 weeks in treatments that receive at least 12 hours of dew. Besides the 32° C. treatments the lowest amount of disease occurs at 28° C. The 48-hour dew period treatment results in disease significantly greater ($P<0.002$) than in 24-hour dew period treatments after 2 weeks at all effective temperatures except 16° C. Minor infections often allow subsequent rebudding from the cotyledonary node or new bud formation in the main root below the potting medium surface. Increasing dew periods result in progressively less shoot tissue available for harvest in inoculated treatments. Fresh weight reduction in shoots correlates well with disease ratings ($r=0.842$, $P<0.0001$). Differences in mean shoot biomass between inoculated and noninoculated plants are significant at all dew periods ($P<0.0001$). Significant differences are found in fresh shoot weight comparisons between all temperatures except between 20° and 24° C. Spore germination rate on water agar is slowest at 16°, 28° and 32° C., and optimal at 24° C. Nearly 100% of the spores germinate within 12 hours at 24° C.

In other experiments, the temperature following incubation in dew is shown to affect disease severity. Four pots, with 15 field bindweed plants each, inoculated at $4\times10^7$ spores of *Phoma proboscis* /ml and four noninoculated pots are placed in dew for 12 hours at each of five temperatures: 16°, 20°, 24°, 28° or 32° C. All pots are placed at a post-dew incubation temperature of 24° C. with a 14 hours photoperiod. Plants from the 16°, 20° and 32° C. dew temperatures given a 24° C. post-dew treatment develop significantly greater disease ($P<0.02$) than 12-hour dew treatments of the corresponding temperatures maintained at the corresponding temperatures after dew. Only the 48-hour dew unchanged post-dew temperature treatments at 16°, 20°, and 24° C. significantly exceed the 12-hour dew, 24° C. post-dew treatment disease ratings. Growth of inoculated field bindweed seedlings is significantly reduced following incubation at all temperatures except 32° C.

EXAMPLE 4

Host Range Specifity Testing

Host specificity determinations are conducted on species with phylogenetic relationships to the family Convolvulaceae, of which *Convolvulus arvensis* is a member, and on species in other families representing economically important species or species that might be exposed during field tests or commercial applications with *Phoma proboscis*. The test includes 141 genera, 228 species, and several varieties of selected species. Of the 46 families tested, 27 are in the subclass Metachlamydeae that includes the Convolvulaceae.

In addition, surface-sterilized tuber seed pieces of six varieties of potato (*Solanum tuberosum*) are inoculated with *Phoma proboscis* and incubated in a humid chamber for 2 weeks at 22° C. without any signs of infection by *Phoma proboscis*.

The conditions imposed for host range tests are those previously determined to be ideal for the fungus to cause disease on field bindweed. Each species is grown to a true leaf stage. Each 7.5 cm diameter pot contains from 1 to 10 plants, depending on the innate size of plants and abundance of seed. One pot of each species is untreated and placed in the dew chamber with treated pots. Three pots of each species are inoculated by spraying with a *Phoma proboscis* spore suspension from one-week-old cultures, adjusted to $1 \times 10^7$ spores per ml, allowing 1.5 ml per pot. Larger plants in large pots are sprayed to runoff. Field bindweed plants are included in each test to confirm virulence of the spore suspension. Plants are placed in a dew chamber at 24° C. for 24 hours, then removed to a growth chamber with a light-/dark cycle of 14 hours 24° C./10 hours 21° C. for 2 weeks. These conditions were previously determined to promote optimum disease development on field bindweed. Plants are observed for symptom development repeatedly throughout the 2-week period, but are rated for symptoms relative to untreated controls after 2 weeks. The rating scale was developed solely for these host range tests.

Ratings range from 1=-no symptoms to 8=-death. Only plants with a rating of 6 (=leaf necrosis) or higher are considered susceptible. Symptoms with lower ratings ranging from flecking to leaf edge necrosis appear to be hypersensitive-like resistance reactions or phytotoxicity common in nonhost interactions with high concentrations of spores. On nonhosts, symptoms appear within 48 to 72 hours after inoculation and do not increase in number or severity with time. Young, succulent tissues develop the phytotoxic symptoms in most cases, while older mature tissues are rarely affected.

Of the 228 species tested only 28 show ratings of 6 or higher and only one of these (*Omphalodes linifolia*) is not of the Convolvulaceae family to which field bindweed (*Convolvulus arvensis*) belongs. Symptoms are not observed in important crops such as cereals, sugar beet, etc. where field bindweed is a problem.

What is claimed is:

1. A method for controlling field bindweed which comprises applying to the weed or the locus thereof a plant growth controlling amount of the fungus *Phoma proboscis* Heiny having the identifying characteristics of ATCC 74032, or a fungus having the identifying characteristics thereof, of a field bindweed controlling mutation thereof.

2. A plant growth controlling composition comprising a plant growth controlling amount of the fungus *Phoma proboscis* Heiny having the identifying characteristics of ATCC 74032, or a fungus having the identifying characteristics thereof, or a field bindweed controlling mutation thereof in admixture with an agriculturally acceptable carrier or adjuvant.

* * * * *